(12) United States Patent
Zhao (10) Patent No.: US 9,001,327 B2
(45) Date of Patent: Apr. 7, 2015

(54) COMPOSITE POLARIZER WITH ADJUSTABLE POLARIZATION ANGLES

(75) Inventor: Guoheng Zhao, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 100 days.

(21) Appl. No.: 13/883,988

(22) PCT Filed: Feb. 14, 2012

(86) PCT No.: PCT/US2012/025130
§ 371 (c)(1),
(2), (4) Date: Jul. 3, 2013

(87) PCT Pub. No.: WO2012/112616
PCT Pub. Date: Aug. 23, 2012

(65) Prior Publication Data
US 2013/0293888 A1    Nov. 7, 2013

Related U.S. Application Data

(60) Provisional application No. 61/442,804, filed on Feb. 15, 2011.

(51) Int. Cl.
| | |
|---|---|
| G01J 4/00 | (2006.01) |
| G02B 27/28 | (2006.01) |
| G02B 5/30 | (2006.01) |
| G01N 21/21 | (2006.01) |
| G01N 21/88 | (2006.01) |
| G01N 21/95 | (2006.01) |

(52) U.S. Cl.
CPC ............ *G02B 27/286* (2013.01); *G02B 5/3066* (2013.01); *G02B 27/283* (2013.01); *G01N 21/21* (2013.01); *G01N 21/8806* (2013.01); *G01N 21/9501* (2013.01); *G01N 2021/8848* (2013.01)

(58) Field of Classification Search
CPC ... G02B 5/3025; G01N 21/9505; G01N 21/88
See application file for complete search history.

(56) References Cited

U.S. PATENT DOCUMENTS

| | | | |
|---|---|---|---|
| 4,612,550 A | 9/1986 | Brucker et al. | |
| 5,225,778 A * | 7/1993 | Chaillout et al. | 324/304 |
| 5,357,342 A | 10/1994 | Decker et al. | |
| 5,457,533 A * | 10/1995 | Wilcken | 356/491 |
| 6,400,739 B1 * | 6/2002 | Auracher | 372/32 |
| 2007/0159602 A1 | 7/2007 | Fergason | |
| 2008/0246948 A1 | 10/2008 | Van Schaik et al. | |
| 2010/0121607 A1 * | 5/2010 | Nabatova-Gabain et al. | 702/172 |

* cited by examiner

*Primary Examiner* — Kara E Geisel
*Assistant Examiner* — Maurice Smith
(74) *Attorney, Agent, or Firm* — Bever, Hoffman & Harms, LLP (57) ABSTRACT

An adjustable, composite polarizer can include first and second plate polarizers and an adjusting apparatus. The adjusting apparatus can adjust a pitch angle and a roll angle for the first and second plate polarizers while maintaining a predetermined, minimal distance between those plates. In this configuration, the adjustable, composite polarizer can provide mirror symmetric polarization with respect to an incident plane while providing the flexibility of any polarization.

24 Claims, 11 Drawing Sheets

COMPOSITE POLARIZER WITH ADJUSTABLE POLARIZATION ANGLES

RELATED APPLICATIONS

This application claims priority of U.S. Provisional Patent Application 61/442,804, entitled "Mirror Symmetric Polarizer With Adjustable Polarization Angle" filed Feb. 15, 2011 and PCT Patent Application PCT/US12/25130, entitled "Composite Polarizer With Adjustable Polarization Angles" filed Feb. 14, 2012.

BACKGROUND OF THE INVENTION

1. Field of the Invention

The present invention relates to a polarizer within an inspection system and in particular to a composite polarizer having a plurality of plate polarizers, each plate polarizer having a predetermined pitch angle and roll angle to provide a desired polarization.

2. Related Art

In general, using a polarizer in the imaging or collection path of a wafer inspection tool can take advantage of the distinctly different polarized scattered light from a wafer surface and from defects to significantly improve detection sensitivity. In a conventional wafer inspection tool, a linear polarizer with a unified polarization across the entire imaging aperture is typically used in the collection path. Note that a linear polarizer can be a reflective polarizer in which an incoming beam is split into a transmitted beam and a reflected beam with perpendicular polarization states, or an absorptive polarizer in which one of the two perpendicular polarizations is absorbed and the other one is transmitted. Reflective polarizers generally have much higher efficiency but need a larger free space because of the large incident angle. Absorptive polarizers are more compact since it can operates at a normal incident angle, but are much less efficient than reflective polarizers because of absorption loss.

Another type of polarizer used in wafer inspection is a linear polarizing cube with a single unified polarization. Notably, this linear polarizing cube has an adjustable polarizer angle, but the polarization is at a constant angle over the entire imaging aperture. Therefore, a linear polarizing cube cannot achieve a maximum signal to noise ratio (SNR). In one embodiment to achieve improved SNR, a linear polarizing cube can be cut diagonally from opposite corners and then reconnected to form the cube. By having multiple reconnected polarizing cubes available in a wafer inspection system, it is possible to have multiple reconnected polarizing cubes of which polarizations are at different pre-determined angles, wherein switching between the reconnected cubes can provide different polarizations. Such a system is complex and bulky, and polarization angles can only be adjusted in a set of discrete steps but not continuously, which makes it difficult to optimize for maximum SNR.

A so-called "pizza pie" polarizer has been used for wafer inspection, wherein this polarizer is formed with multiple absorptive linear polarizers (each shaped like a pizza pie piece) to provide a circularly symmetric polarization arrangement. These linear polarizers have either polarization aligned in a radial direction or in a tangential direction. One of the disadvantages of the conventional "pizza pie" polarizers is the low efficiency due to the use of absorptive polarizers.

Unfortunately, a need still exists for a polarizer that has adjustable polarization angles while remaining mirror symmetric with a plane, e.g. the incident plane of a wafer inspection system with oblique illumination.

SUMMARY OF THE INVENTION

An adjustable, composite polarizer can include first and second plate polarizers and an adjusting apparatus. The adjusting apparatus can adjust a pitch angle and a roll angle for the first and second plate polarizers while maintaining a predetermined distance between those plate polarizers. In this configuration, the adjustable, composite polarizer can provide mirror symmetric polarization with respect to an incident plane while providing the flexibility of any polarization and maintaining a minimal gap between the two parallel, abutting edges of the two plate polarizers.

In one embodiment, the adjusting apparatus can include hinges attached to abutting edges of two plate polarizer frames, each of which secures one plate polarizer. The frames can be open at the sides where the parallel, abutting edges of two polarizer plates meet, and the hinges can be located on the sides of frames that are outside the collection aperture to minimize blockage of collection aperture. An assembly frame can include a plurality of hinge rods. One set of hinge rods can be attached to the assembly frame to provide pitch angle adjustment. Another hinge rod can be used with an arc track to provide roll angle adjustment, wherein turning this hinge rod either folds the plates apart or together (equally). One or more motors can be connected to the hinge rods to provide motorized adjustment of the pitch and roll angles. In one embodiment, one motor can be used to turn the set of hinge rods for pitch adjustment, while another motor can be used to turn the hinge rod for roll adjustment. The adjusting apparatus can be configured to communicate with a processor, which can compute the pitch angle and the roll angle based on a desired polarization angle. In one embodiment, the processor can interface with a look-up table, which can store a plurality of desired polarization angles and their corresponding pitch and roll angles.

Another adjustable, composite polarizer can include a plurality of plate polarizers and an adjusting apparatus. The adjusting apparatus can adjust a pitch angle and a roll angle for each of the plurality of plate polarizers while maintaining a predetermined distance between each pair of those plate polarizers. The plurality of plate polarizers can form a tangential polarizer or a radial polarizer.

A method of adjusting polarization in an optical system is also described. In this method, a first desired polarization can be designated. First pitch angles and first roll angles for a plurality of plate polarizers to achieve the first desired polarization can be determined. The plurality of plate polarizers can then be adjusted to the first pitch angles and the first roll angles.

In one embodiment, the method further includes determining a targeted defect type for inspection using the optical system. At that point, the first desired polarization can be determined based on the targeted defect type. In another embodiment, the method can further include determining a wafer type for inspection using the optical system. At that point, the first desired polarization can be determined based on the wafer type.

In one embodiment, determining the first pitch angles and the first roll angles can include computing the first pitch angles and the first roll angles. In another embodiment, determining the first pitch angles and the first roll angles includes finding the first pitch angles and the first roll angles in a look-up table based on the first desired polarization.

The method can further include designating a second desired polarization. Then, second pitch angles and second roll angles of a plurality of plate polarizers can be determined to achieve the second desired polarization. At that point, the plurality of plate polarizers can be adjusted from the first pitch angles and the first roll angles to the second pitch angles and the second roll angles.

Another method of providing polarization in an optical system is also described. In this method, a plurality of plate polarizers can be positioned, each polarizer abutting at least one other polarizer. An adjusting apparatus can be configured to provide a predetermined pitch and roll to each polarizer.

Yet another method for providing polarization in an optical system is described. In this method, a plurality of plate polarizers can be positioned, each polarizer abutting at least one other polarizer. A predetermined pitch and roll can be provided to each polarizer.

An inspection system is also described. This inspection system includes a light source, an illumination path for directing light from the light source onto a test object, a collection path for directing scattered light from the test object, and a detector for receiving the collected light. Notably, the collection path can include an adjustable, composite polarizer as described herein. An adjusting apparatus can be connected to the adjustable, composite polarizer. A processor or look-up table can be used for controlling the adjusting apparatus.

DETAILED DESCRIPTION OF THE INVENTION

Polarized light detection can significantly improve defect sensitivity for both pattern and bare (un-pattern) wafer inspection tools. For example, a state of the art polarization mask for bare wafer inspection has been demonstrated to shown signal to noise improvement of over 20×.

Figure 1:
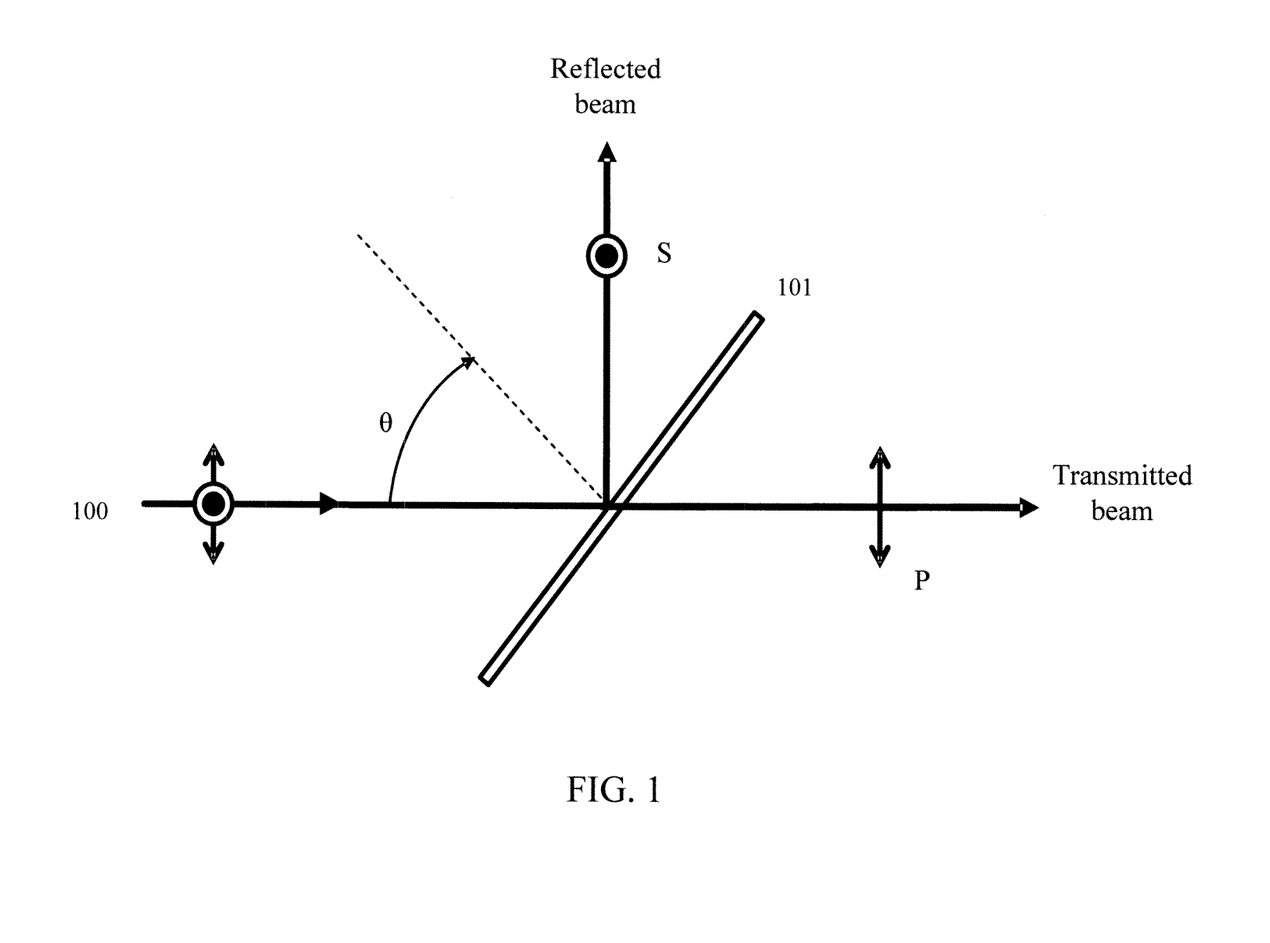
FIG. 1 illustrates the principles of a reflective plate polarizer.

Referring to FIG. 1, a plane of incidence refers to a plane formed by a propagation direction of the incident light beam 100 and a surface normal of a thin film plate polarizer 101. The incident angle θ is angle between incoming light beam and surface normal of the plate polarizer 101. Typically, the polarization of the incident beam can be decomposed into two perpendicular components namely P and S, wherein P polarization is parallel to the plane of incidence and S polarization is perpendicular to that plane. S polarization component of the incident beam is reflected and P component is transmitted by the plate polarizer.

Generally, in a wafer inspection system using directional oblique illumination, the illumination polarization is either P or S, which is mirror symmetric with respect to the incident plane. Other polarizations of illumination can also be considered mirror symmetric for samples that are less sensitive to phase of polarization include circular or elliptical with one axis of ellipse being parallel to the incident plane. As a result, the polarization distribution in the collection pupil plane of an inspection system is mirror symmetric with respect to the incident plane, but not necessarily parallel or perpendicular to the incident plane.

In accordance with one aspect of an improved polarizer, a linear polarizer can provide mirror symmetric polarization with respect to the incident plane as well as an adjustable polarization angle. As described in further detail below, this improved polarizer can be formed with multiple plate polarizers, each of which can be adjusted to a predetermined pitch angle and roll angle combination to yield a desired polarization. This adjustable, composite polarizer can be used in a bare wafer inspection tool, a pattern wafer inspection tool, or any other inspection tool where polarization is provided in the collection path.

Figure 2A:
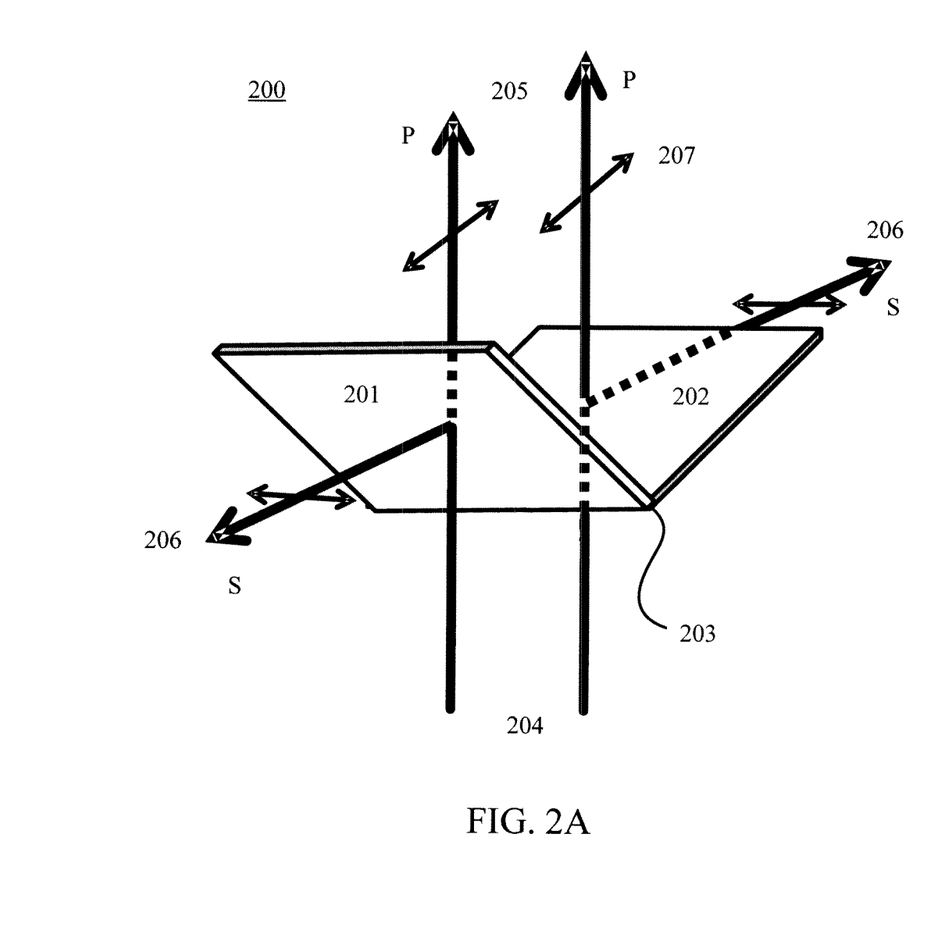
FIG. 2A illustrates an exemplary adjustable, composite polarizer.

FIG. 2A illustrates an exemplary adjustable, composite polarizer 200. In this embodiment, polarizer 200 can include two rectangular plate polarizers 201 and 202, which have parallel, abutting edges 203 (a small gap between the edges of the two plate polarizers provides freedom of motion) so that plate polarizers 201 and 202 cover the whole collection aperture. These abutting edges 203 form a common axis, wherein polarizers 201 and 202 can rotate around this common axis (called a roll angle herein). Incoming light beams 204 (shown as two light rays for simplicity) are separated by composite polarizer 200 into transmitted beams 205 (P polarization) and reflected beams 206 (S polarization). Double-headed arrows 207 in FIG. 2A and its legend represent the polarization orientation of the light beams that the arrows intersect.

Figure 2B:
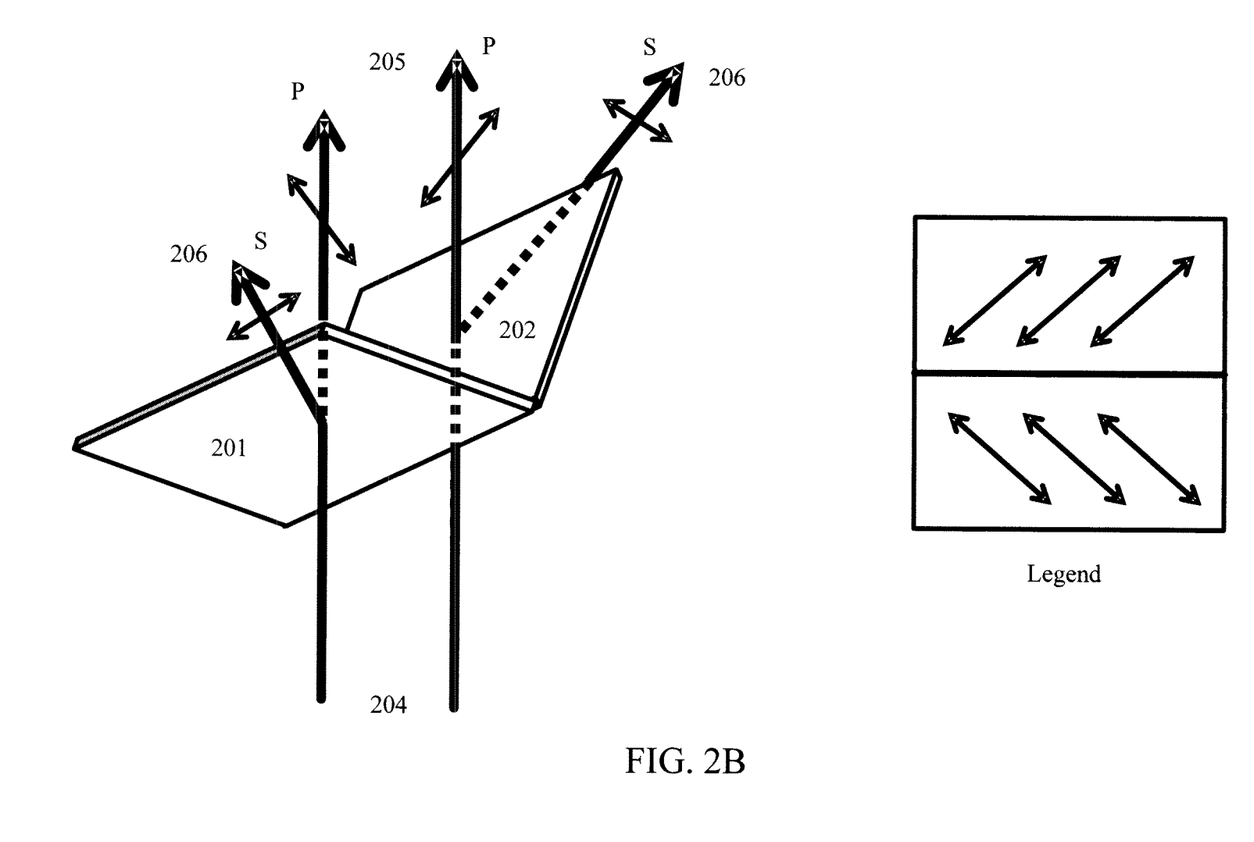
FIG. 2B illustrates how changing the pitch and roll angles of the adjustable, composite polarizer of FIG. 2A changes the resulting polarization.
Figure 2C:
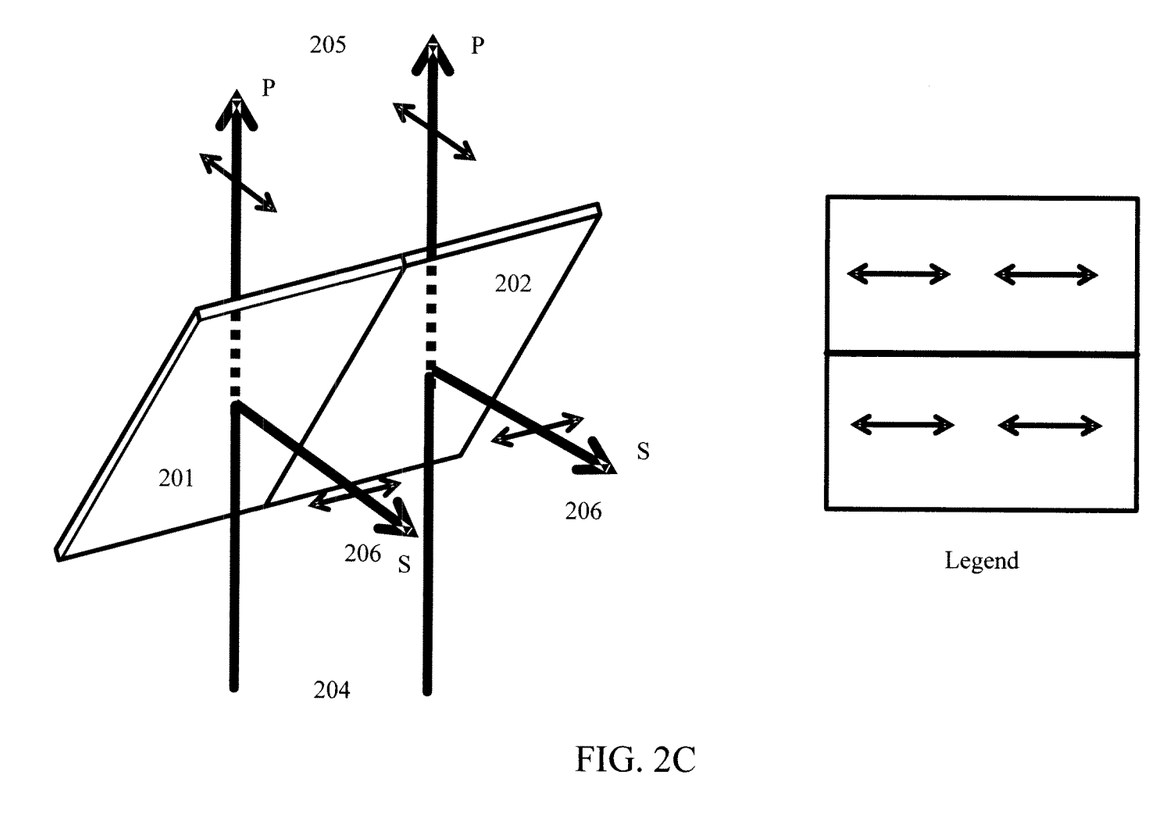
FIG. 2C illustrates how changing the pitch and roll angles of the adjustable, composite polarizer of FIG. 2A changes the resulting polarization.

FIGS. 2A, 2B, and 2C illustrate composite polarizer 200 at different pitch and roll angles, and their resulting polarizations. To adjust the direction of polarization of transmitted beam 205 and 207, the incident plane on each plate polarizer need to be rotated around the axis of incoming beam 204. This is demonstrated by comparing FIGS. 2A and 2B. In FIG. 2A, edges 203 are perpendicular to incoming beam 204, thereby resulting in polarizations of transmitted light from both plates being perpendicular to the common axis and edges 203. In contrast, in FIG. 2B, the pitch angle of edges 203 is increased to cause the incident plane of plates 201 and 202 to rotate in opposite direction around the incoming beam direction, thereby causing the transmitted P polarization to also rotate around the incoming beam direction. However, note that increasing the pitch angle alone also changes the incident angle on plates 201 and 202, which results in degraded purity of transmitted polarization because of the limited acceptance angle of plate polarizers.

To keep the incident angle constant while the pitch angle changes, the roll angle of plates 201 and 202 need to be adjusted to compensate for the change of incident angles caused by the change of pitch angle. The combination of pitch and roll angle adjustment changes the polarization to a desired direction, while maintaining the polarization mirror symmetry. Moreover, maintaining a minimal gap between the two parallel, abutting edges of the two plate polarizers can provide maximum coverage of collection aperture. In one embodiment, an additional mask (not shown for simplicity) may be used to block the small amount of light leaked through the gap between two plate polarizers.

FIG. 2C illustrates one of the extreme angles of pitch and roll adjustment, where the mirror symmetric polarization angles has been adjusted from perpendicular to the common axis (FIG. 2A) to parallel to the common axis (formed by parallel, abutting edges 203). While the range of polarization angle adjustment shown from FIG. 2A to FIG. 2C is only 90 degrees, the total range of polarization angle adjustment can be 180 degrees (from −90 degrees to +90 degrees) since the pitch angle can also be adjusted in the opposite direction shown in FIG. 2B.

Figure 3A:
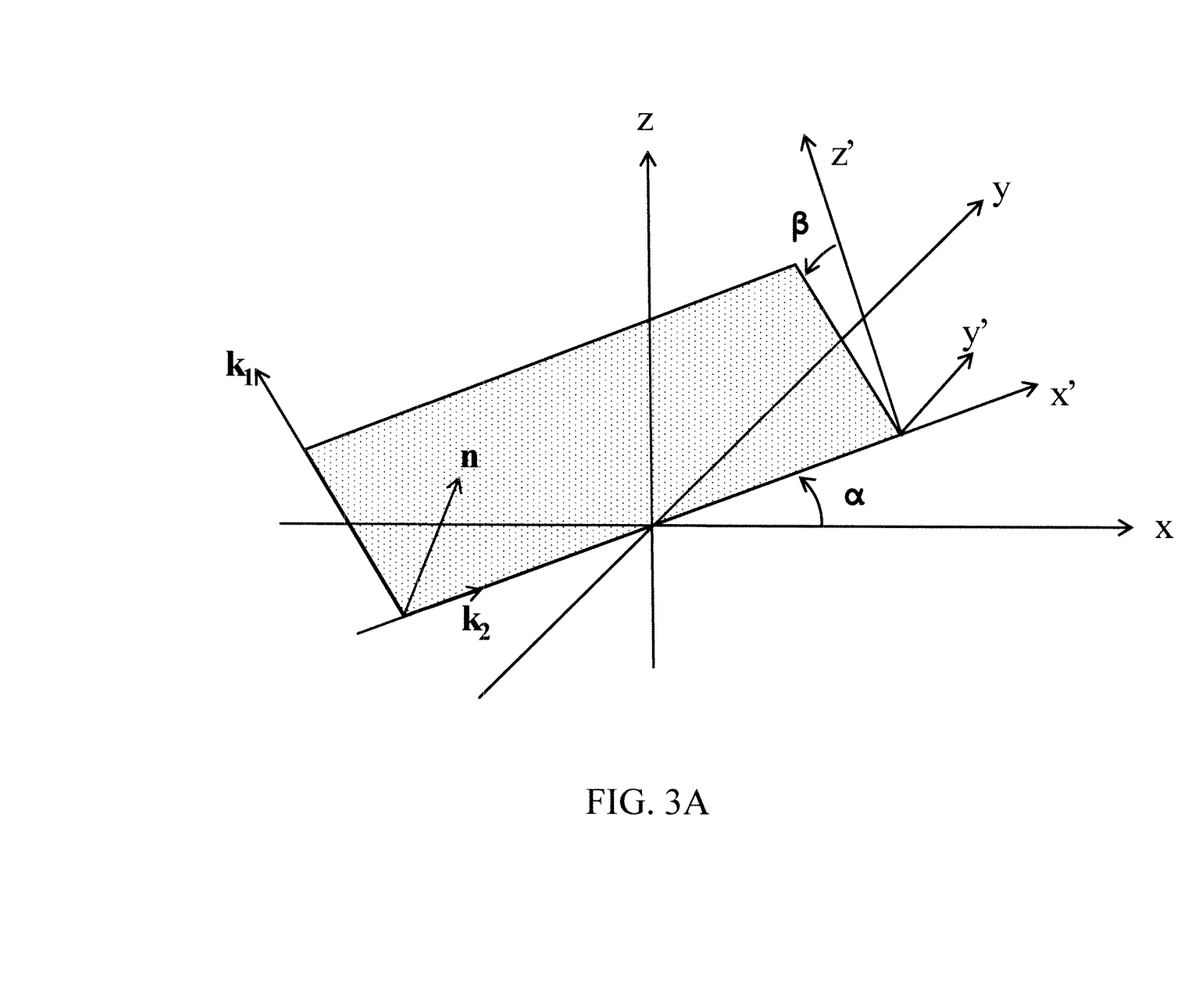
FIG. 3A illustrates various variables associated with a polarizer plate.
Figure 3B:
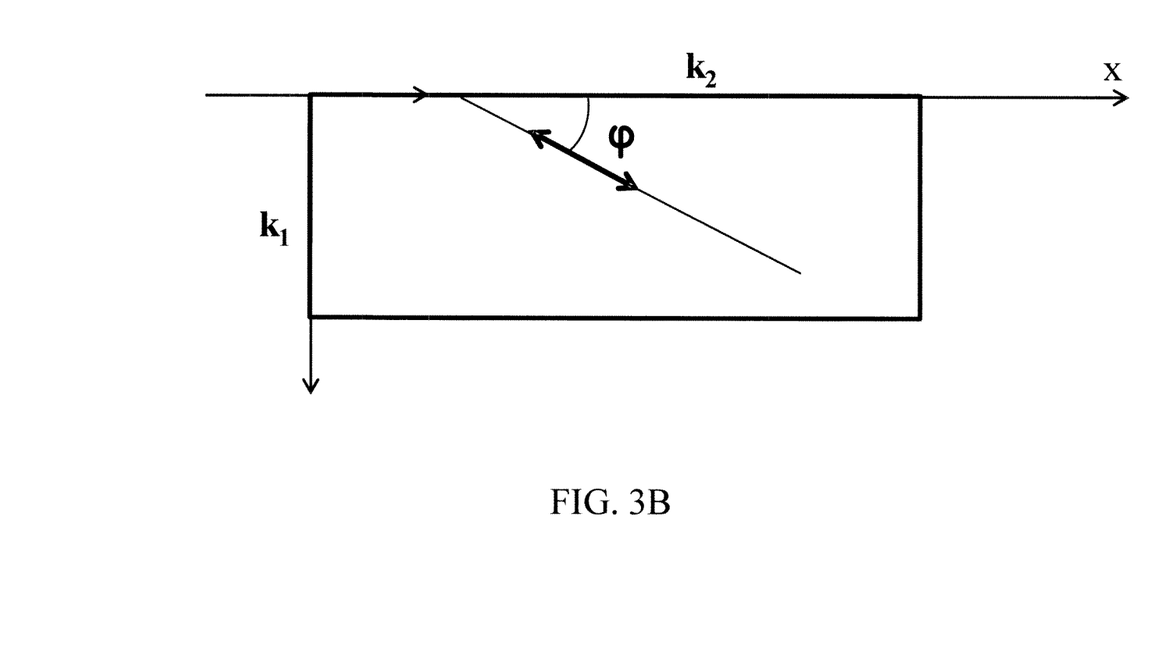
FIG. 3B illustrates a top view of the polarizer plate shown in FIG. 3A.

FIGS. 3A and 3B further explain in detail the principle of mirror symmetric polarization angle adjustment through coordinated adjustments of pitch and roll angles of polarization plates as demonstrated above, by illustrating various angles, edges, axes, and coordinates for a single plate polarizer. As used herein, α is a pitch angle of the polarizer, β is a ½ open angle, also called the roll (wherein 2β defines the angle between the two polarizers, e.g. polarizers 201 and 202), θ is the incident angle of incoming light beams 204 (see, e.g. FIG. 1), ϕ is a desired polarization angle (shown in FIG. 3B, which is a top view of FIG. 3A), $k_1$ is a unit vector parallel to the plate short edge, $k_2$ is a unit vector parallel to the plate long edge, and n is a plate surface normal defined by $k_1 \times k_2$.

Note that the above-listed variables are used to describe the orientation of a plate in general, and apply to both polarizers 201 and 202. Axes xyz can be characterized as global reference coordinates, whereas axes x'y'z' are local reference coordinate defined by a rotation of xyz around y axis by the pitch angle α. Axis z is the collection optical axis (i.e. the direction of incoming beam), and xz (or x'z') is also the incident plane of an inspection system. Notably, polarizers 201 and 202 are symmetric with respect to the x'z' plane (see, e.g. FIG. 3A), thereby forming a mirror symmetric polarizer.

In accordance with one aspect of correctly adjusting polarizers 201 and/or 202 to obtain the desired polarization angle ϕ, and at the same time one of the plate edge (x' axis) must be kept within the xz plane so that polarizers 201 and 202 maintain abutting edges 203 parallel to one another during polarizer angle adjustment, the following equations can provide an analytical solution. Note that generally a plate polarizer is designed to be used at a fixed incident angle (e.g. 45 degrees for convenience of alignment, or a Brewster angle for better performance). The tolerance of this incident angle θ is typically a few degrees, larger deviation from the designed incident angle degrades the purity of transmitted polarization. Therefore, this incident angle needs to be maintained constant to a high degree of accuracy when the pitch and roll angles of the two plate polarizers are adjusted. For a desired transmission polarization angle ϕ, the pitch and roll angles of the plate polarizers of the adjustable, composite polarizer can be calculated using the equations below.

For a desired polarization angle ϕ, pitch α and roll β can be computed by using equations (1)-(12) below.

$$x' = \cos\alpha x + \sin\alpha z \quad \text{Eq. (1)}$$

$$y' = y \quad \text{Eq. (2)}$$

$$z' = -\sin\alpha x + \cos\alpha z \quad \text{Eq. (3)}$$

$$k_1 = -\sin\beta y' + \cos\beta z' \quad \text{Eq. (4)}$$
$$= -\cos\beta \sin\alpha x - \sin\beta y + \cos\beta \cos\alpha z$$

$$k_2 = x' \quad \text{Eq. (5)}$$
$$= \cos\alpha x + \sin\alpha z$$

$$n = k_1 \times k_2 \quad \text{Eq. (6)}$$

$$n = \sin\theta\cos\varphi x + \sin\theta\sin\varphi y + \cos\theta z \quad \text{Eq. (7)}$$

$$k_1 \times k_2 = -\sin\alpha\beta x + \cos\beta y + \cos\alpha\sin\beta z \quad \text{Eq. (8)}$$

$$\cos\theta = \cos\alpha\sin\beta \quad \text{Eq. (9)}$$

$$\tan\varphi = -\frac{1}{\sin\alpha\tan\beta} \quad \text{Eq. (10)}$$

$$\tan\alpha = -\tan\theta\cos\varphi \quad \text{Eq. (11)}$$

$$\cos\beta = \sin\theta\sin\varphi \quad \text{Eq. (12)}$$

Using the above-described adjustable, composite polarizer and computations, the transmitted polarization can be continuously adjusted while maintaining mirror symmetry with respect to incident plane. As noted above, the transmitted polarization is parallel to the incident plane while reflected polarization is perpendicular to the incident plane. Therefore, the transmitted polarization can be adjusted by rotating the composite polarizer around the axis of incident beam while maintaining a constant incident angle for a single plate polarizer. However, to achieve mirror symmetric polarization while maintaining parallel, abutting edges of two plate polarizer to keep a minimal gap between them, both pitch and roll angles have to be adjusted in a relationship described in equations 1-12.

To mechanically provide the pitch and roll angles to the plate polarizers, an adjusting apparatus can be used. In one embodiment shown in FIG. 2D, an adjusting apparatus 200 can include hinges 221 attached to abutting edges of two plate polarizer frames 222, each of which secures one plate polarizer 223. Plate polarizer frames 222 provide the necessary mechanical mounting and adjusting interface while holding plate polarizers 223 (which are typically made from glass materials that are not suitable for mechanical interface). In one preferred embodiment, plate polarizer frames 222 can be open on the sides where the parallel, abutting edges of plate polarizers 223 meet to minimize blockage of the collection aperture. Note that plate polarizer frames 222 and plate polarizers 223 are larger than the collection aperture, which can be from a few millimeters to more than 100 millimeters. Hinges 221 are preferable located near the edges of plate polarizer frames 222 and would therefore be outside the collection aperture to minimize blockage of collection aperture. The rotation axis of hinges 221 coincides with the parallel, abutting edges 203 of plate polarizers 223, which also determines the mounting position of plate polarizers 223 on plate polarizer frames 222. Notably, this configuration can reduce and minimize the variation of the gap between plate polarizers 223 while pitch and roll angles change. The distance between plate polarizers 223, i.e. between parallel, abutting edges 203, is preferably minimized, wherein a minimal predetermined distance can be determined by the thickness of plate polarizers 223.

Figure 2D:
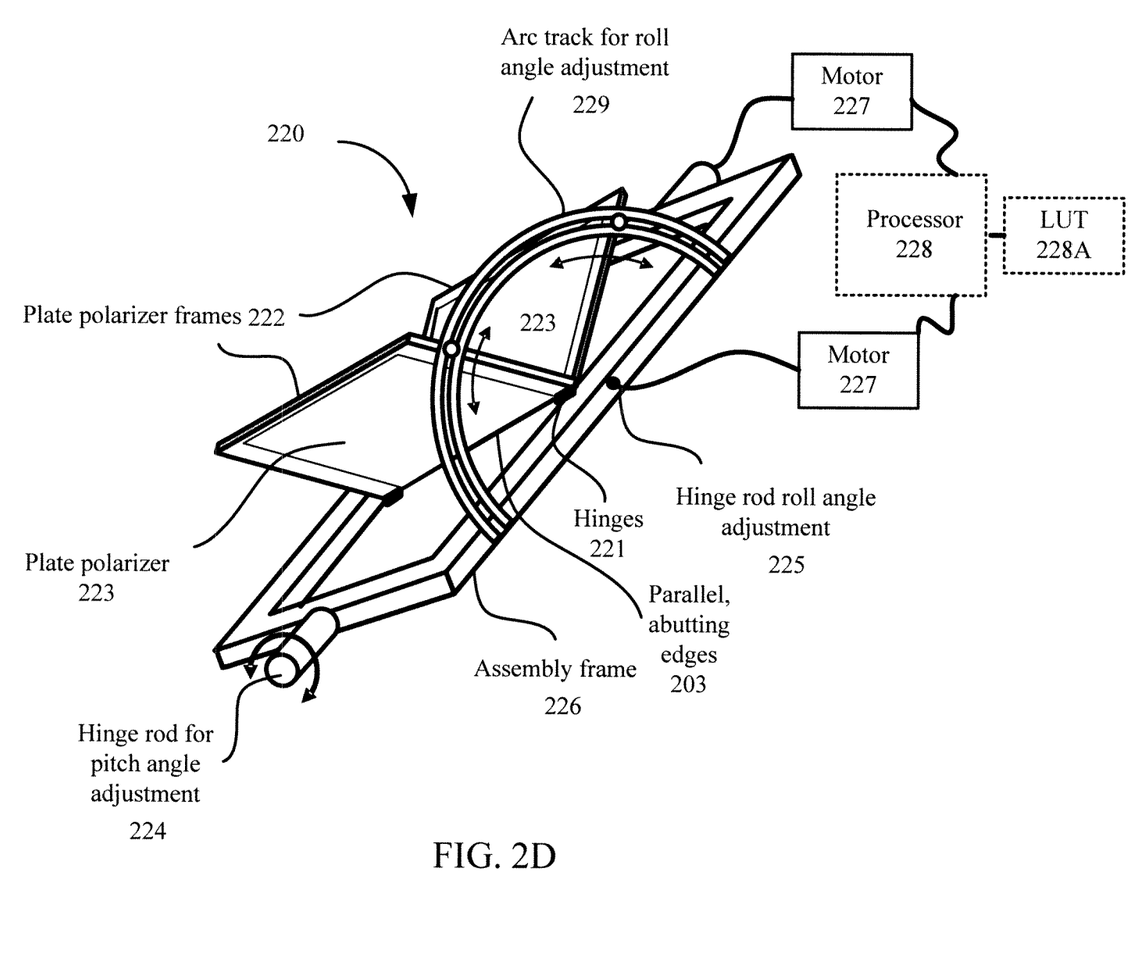
FIG. 2D illustrates an exemplary adjustment apparatus for providing the pitch and roll angles to the plate polarizers.

An assembly frame 226 can include a plurality of hinge rods. One set of hinge rods 224 can be attached to assembly frame 226 to provide pitch angle adjustment. Another hinge rod 225 can be used with an arc track 229 to provide roll angle adjustment, wherein moving this hinge rod 225 along the arc track 229 either folds the plates apart or together (equally) from the common axis. One or more motors 227 can be connected to the hinge rods to provide motorized adjustment of the pitch and roll angles. In one embodiment, one motor can be used to turn the set of hinge rods 224 for pitch adjustment, while another motor can be used to move hinge rod 225 for roll adjustment.

Figure 4:
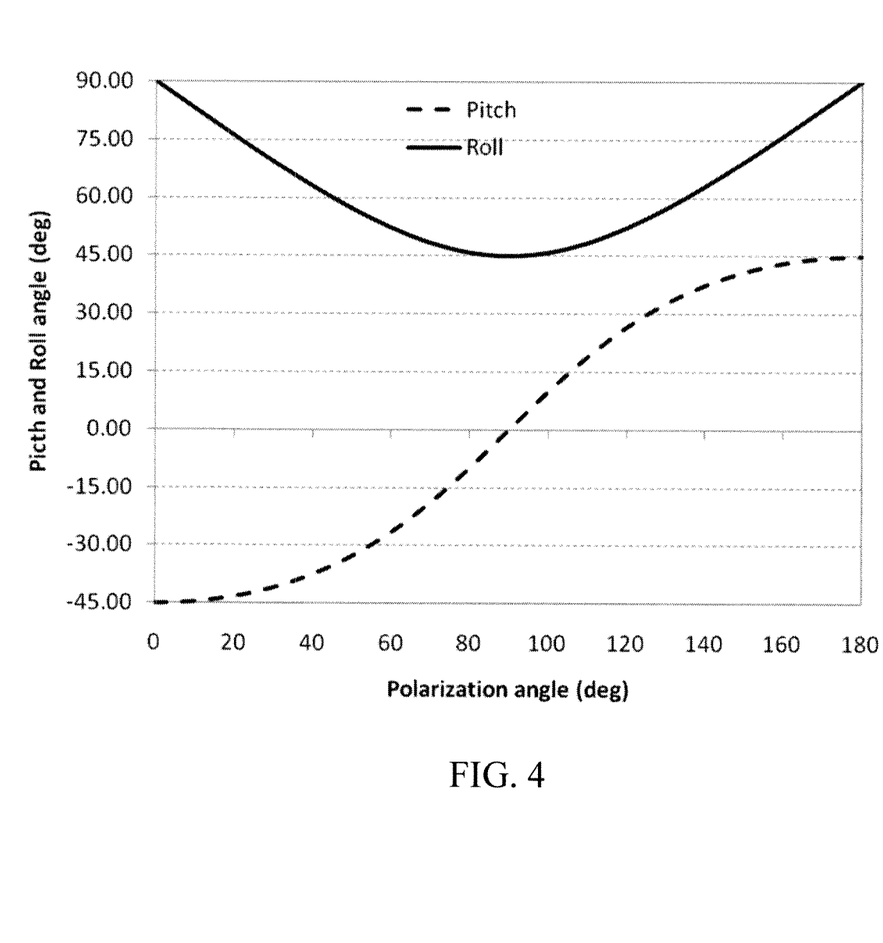
FIG. 4 illustrates pitch and roll as functions of the polarization angle for a plate polarization with an incident angle of 45 degrees.

Adjusting apparatus 200 can communicate with a processor 228 for computing the pitch angle and the roll angle based on a desired polarization angle. In one embodiment, processor 228 can interface with a look-up table (LUT) 228A, which can store a plurality of desired polarization angles and their corresponding pitch and roll angles, thereby freeing up computing resources of processor 228. In this case, the LUT can be organized by polarization angles with their corresponding pitch and roll angles. FIG. 4 illustrates exemplary pitch and roll angles as a function of the polarization angle, assuming the incident angle of the plate polarization is 45 degrees.

Figure 5A:
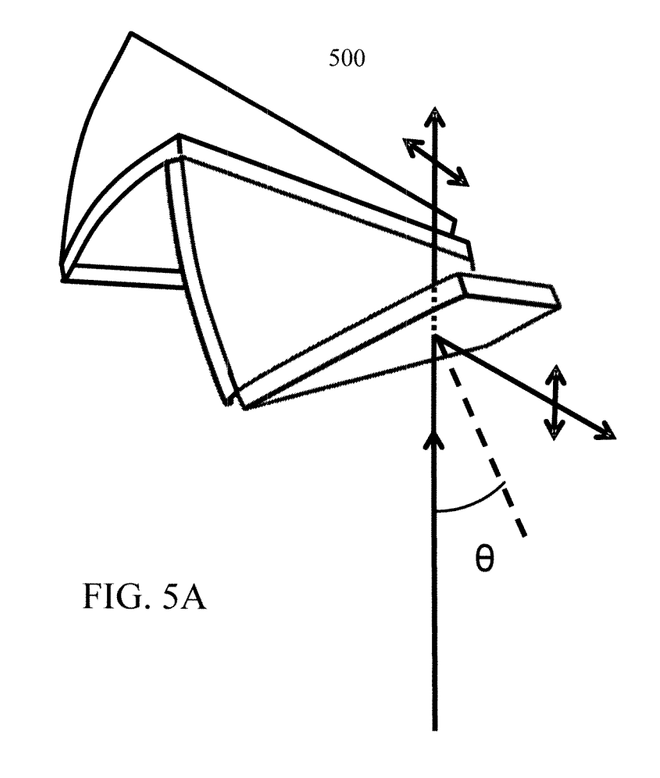
FIGS. 5A and 5B illustrate perspective and top views of an exemplary tangential polarizer.
Figure 5B:
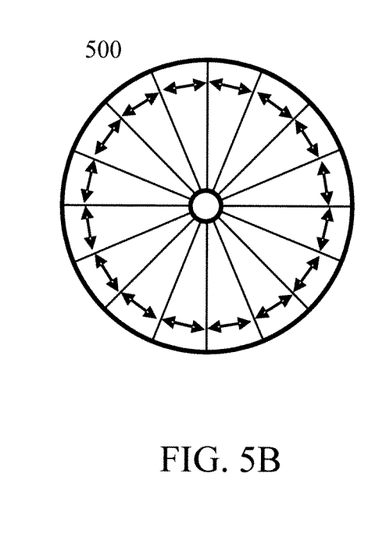
Figure 6A:
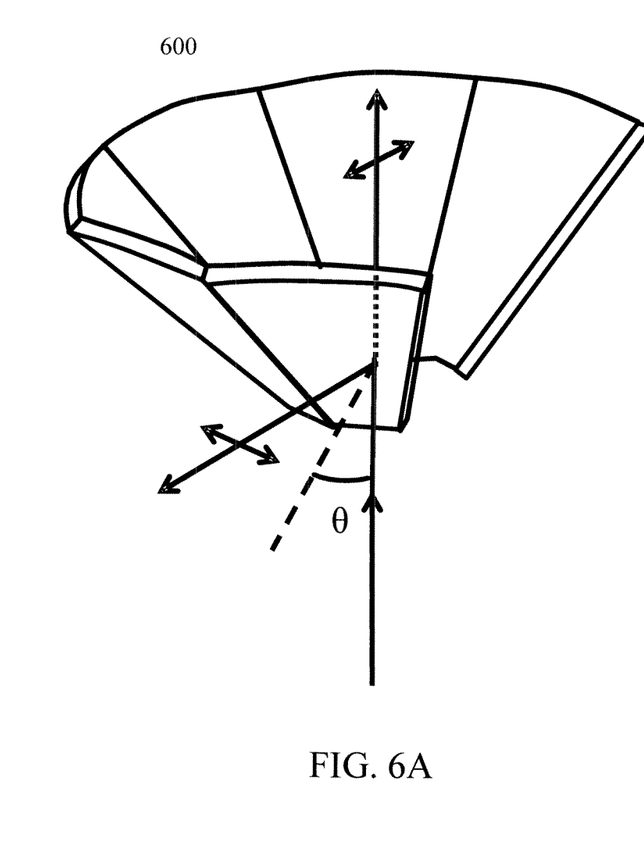
FIGS. 6A and 6B illustrate perspective and top views of an exemplary radial polarizer.
Figure 6B:
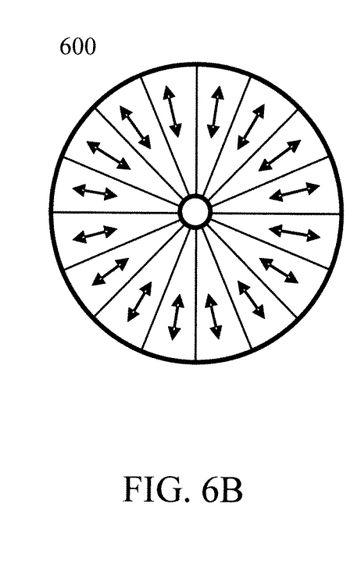

In one embodiment, more than two polarizers can be used to form the adjustable, composite polarizer. For example, FIGS. 5A and 5B illustrate perspective and top views of a tangential composite polarizer 500 that can use the same concepts taught above. FIGS. 6A and 6B illustrate perspective and top views of a radial composite polarizer 600 that can use the same concepts taught above. Note that an exemplary numbers of polarizers in some embodiments may be from 8-32, although other embodiments may have more or fewer plates. Note that increasing the number of polarizers results in polarizations that more closely approximate a continuously-varying polarization angle. However, increasing the number of polarizers may also increase total gap distance between those polarizers, thereby resulting in some reduction of polarizer transmission efficiency. In one embodiment, the above-described plate polarizers of the adjustable, composite polarizer can be fabricated using thin film linear polarizer plates that can provide transmission of greater than 90%.

Note that any of the above embodiments can be fixedly secured into a single polarization using known techniques including, but not limited to, gluing and mechanical mounting frames. These non-adjustable embodiments can still provide the following advantages. The polarization is circularly symmetric with respect to the collection aperture, rather than mirror symmetric with respect to the incident plane. Such polarizations can provide optimum SNR for the cases where polarization of light collected from sample is circularly symmetric. Using a thin film plate polarizer has the advantage of very low loss comparing to using absorptive polarizer such as wire grid polarizers.

Figure 7:
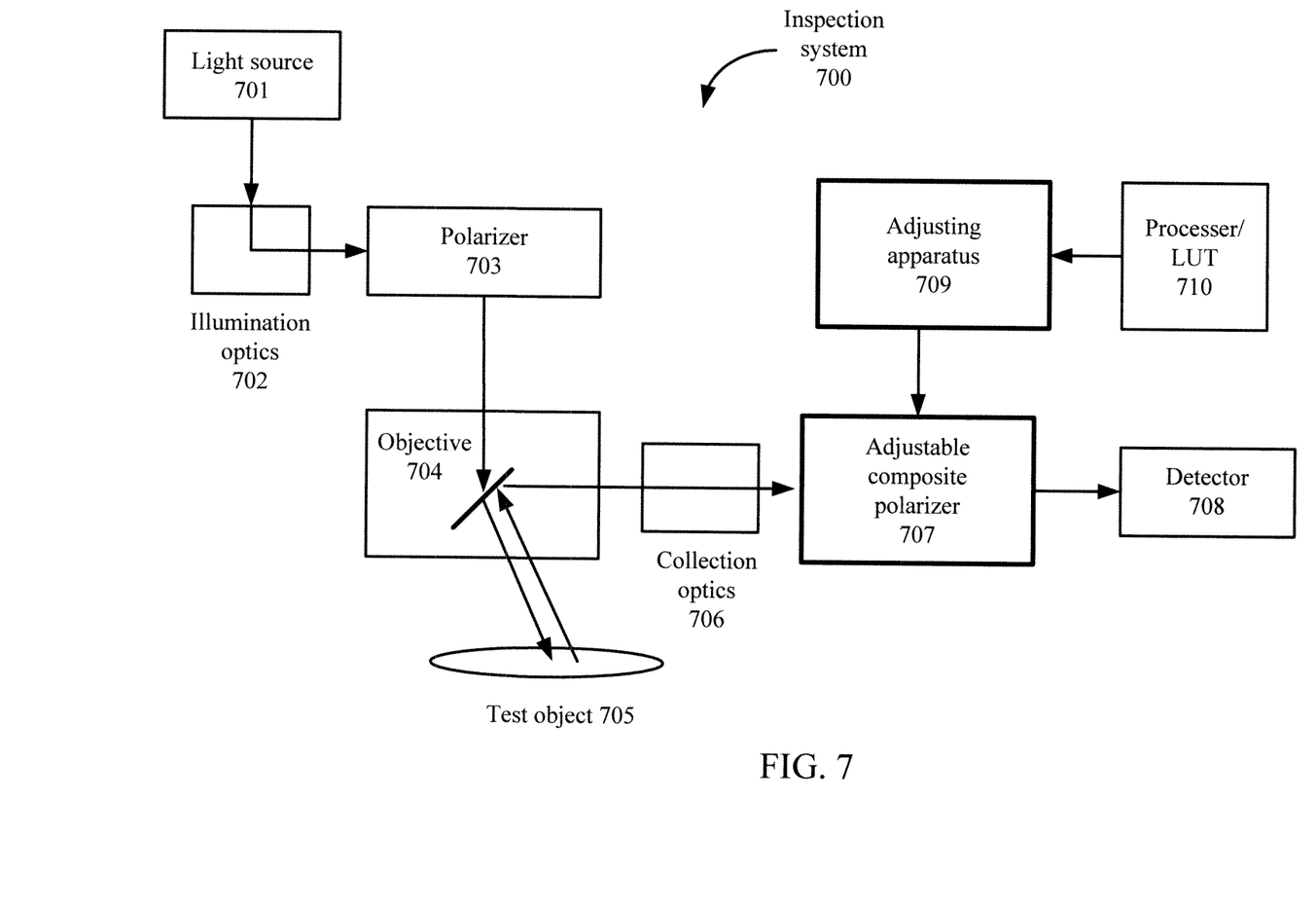
FIG. 7 illustrates a simplified inspection system including an adjustable composite polarizer.

FIG. 7 illustrates an exemplary inspection system 700 including an adjustable, composite polarizer 706. In this system, light from a source 101 (e.g. a laser) is directed onto a test object 705 (e.g. a wafer or an integrated circuit) using illumination optics 702, a polarizer 703, and an objective 704. Scattered or reflected light from test object 705 is directed to a detector 708 using collection optics 706 and adjustable, composite polarizer 707.

In this embodiment, the polarization of the collected light can be controlled in the collection path. Specifically, adjustable composite polarizer 706 can control the polarization of light in the collection path, which includes collection optics 707 and adjustable, composite polarizer 706. Adjustable, composite polarizer 706 can be dynamically adjusted using an adjusting apparatus 709. In one embodiment, adjusting apparatus 709 can include components similar to those of adjusting apparatus 220 (FIG. 2D) Adjusting apparatus 709 can be controlled by a processor 710, which can either calculate the appropriate pitch and roll angles for the plurality of plate polarizers or can find the appropriate angles in a look-up table (LUT) based on the desired polarization. With the correct polarization, a larger concentration of the electric field may be localized at a specific layer of test object 705, thereby making the inspection system more sensitive to targeted defects of interest while suppressing background noise.

Adjustable, composite polarizer 706 can advantageously provide a polarization angle that is mirror symmetric with respect to a plane, typically the incident plane of oblique illumination. As discussed above, the angle of polarization can be dynamically adjusted. When the illumination polarization is either P or S, the polarization of scattered light is mirror symmetric with respect to the incident plane. Notably, to maximize the defect signal, the collection polarization needs to be mirror symmetry while its angle can be adjusted and therefore optimized for different wafers and defect types.

The various embodiments of the structures and methods of this invention that are described above are illustrative only of the principles of this invention and are not intended to limit the scope of the invention to the particular embodiments described. Thus, the invention is limited only by the following claims and their equivalents.

The invention claimed is:

1. An adjustable, composite polarizer comprising:
   a first plate polarizer;
   a second plate polarizer; and
   an adjusting apparatus including a first adjustment mechanism that adjusts a pitch angle and a second adjustment mechanism that adjusts a roll angle for the first and second plate polarizers while maintaining a predetermined distance between the first and second plate polarizers.

2. The adjustable, composite polarizer of claim 1, wherein the adjusting apparatus includes:
   a first plate polarizer frame;
   a second plate polarizer frame; and
   a plurality of hinges attached to abutting edges of the first and second plate polarizer frames, the first plate polarizer frame securing the first plate polarizer and the second plate polarizer frame securing the second plate polarizer.

3. The adjustable, composite polarizer of claim 2, wherein the adjusting apparatus further includes:
   an assembly frame;
   a plurality of hinge rods; and
   an arc track,
   wherein the first adjustment mechanism includes one set of hinge rods attached to the assembly frame to provide pitch angle adjustment, and the second adjustment mechanism includes another hinge rod used with the arc track to provide roll angle adjustment.

4. The adjustable, composite polarizer of claim 3, wherein the adjusting apparatus further includes one or more motors connected to the hinge rods to provide motorized adjustment of the pitch and roll angles.

5. The adjustable, composite polarizer of claim 1, wherein the adjusting apparatus is configured to communicate with a processor, which computes the pitch angle and the roll angle based on a desired polarization angle.

6. The adjustable, composite polarizer of claim 5, wherein the processor interfaces with a look-up table for storing a plurality of desired polarization angles and their corresponding pitch and roll angles.

7. An adjustable, composite polarizer comprising:
a plurality of plate polarizers; and
an adjusting apparatus including a first adjustment mechanism that adjusts a pitch angle and a second adjustment mechanism that adjusts a roll angle for each of the plurality of plate polarizers while maintaining a predetermined distance between each pair of the plurality of plate polarizers.

8. The adjustable, composite polarizer of claim 7, wherein the adjusting apparatus includes:
a plurality of plate polarizer frames, each polarizer frame securing one plate polarizer; and
a plurality of hinges attached to abutting edges of the plurality of plate polarizer frames.

9. The adjustable, composite polarizer of claim 8, wherein the adjusting apparatus further includes;
an assembly frame;
a plurality of hinge rods; and
an arc track,
wherein the first adjustment mechanism includes one set of hinge rods attached to the assembly frame to provide pitch angle adjustment, and the second adjustment mechanism includes another hinge rod used with the arc track to provide roll angle adjustment.

10. The adjustable, composite polarizer of claim 9, wherein the adjusting apparatus further includes one or more motors connected to one or more of the plurality of hinge rods to provide motorized adjustment of the pitch and roll angles.

11. The adjustable, composite polarizer of claim 7, wherein the adjusting apparatus is configured to communicate with a processor, which computes the pitch angle and the roll angle based on a desired polarization angle.

12. The adjustable, composite polarizer of claim 11, wherein the processor interfaces with a look-up table for storing a plurality of desired polarization angles and their corresponding pitch and roll angles.

13. The adjustable, composite polarizer of claim 7, wherein the plurality of plate polarizers form a tangential polarizer.

14. The adjustable, composite polarizer of claim 7, wherein the plurality of plate polarizers form a radial polarizer.

15. A method of adjusting polarization in an optical system, the method comprising:
designating a first desired polarization;
determining first pitch angles and first roll angles for a plurality of plate polarizers to achieve the first desired polarization; and
adjusting the plurality of plate polarizers to the first pitch angles using a first adjustment mechanism and the first roll angles using a second adjustment mechanism.

16. The method of claim 15, further including:
determining a targeted defect type for inspection using the optical system; and
determining the first desired polarization based on the targeted defect type.

17. The method of claim 15, further including:
determining a wafer type for inspection using the optical system; and
determining the first desired polarization based on the wafer type.

18. The method of claim 15, wherein determining the first pitch angles and the first roll angles includes computing the first pitch angles and the first roll angles.

19. The method of claim 15, wherein determining the first pitch angles and the first roll angles includes finding the first pitch angles and the first roll angles in a look-up table based on the first desired polarization.

20. The method of claim 15, further including:
designating a second desired polarization;
determining second pitch angles and second roll angles of the plurality of plate polarizers to achieve the second desired polarization; and
adjusting the plurality of plate polarizers from the first pitch angles and the first roll angles to the second pitch angles and the second roll angles.

21. A method of providing polarization in an optical system, the method comprising:
positioning a plurality of plate polarizers, each plate polarizer abutting at least one other plate polarizer; and
configuring an adjusting mechanism using a first adjustment mechanism configured to provide a predetermined pitch and using a second adjustment mechanism configured to provide a predetermined roll angle to each plate polarizer.

22. A method for providing polarization in an optical system, the method comprising:
positioning a plurality of plate polarizers, each plate polarizer abutting at least one other plate polarizer; and
providing a predetermined pitch and roll to each plate polarizer.

23. An inspection system comprising:
a light source;
an illumination path for directing light from the light source onto a test object;
a collection path for directing scattered light from the test object; and
a detector for receiving the collected light,
wherein the collection path includes an adjustable, composite polarizer including
a plurality of plate polarizers; and
an adjusting apparatus including a first adjustment mechanism that adjusts a pitch angle and a second adjustment mechanism that adjusts a roll angle for each of the plurality of plate polarizers while maintaining a predetermined distance between each pair of the plurality of plate polarizers.

24. The inspection system of claim 23, further including a processor configured to control the adjusting apparatus.

* * * * *